(12) United States Patent
Luan et al.

(10) Patent No.: US 12,370,135 B2
(45) Date of Patent: Jul. 29, 2025

(54) ANHYDROUS COMPOSITION FOR CARING FOR AND/OR MAKING UP KERATIN MATERIALS

(71) Applicant: L'OREAL, Paris (FR)

(72) Inventors: Tu Luan, Shanghai (CN); Di Wu, Shanghai (CN); Chunyan Lei, Shanghai (CN); Saijuan Ni, Shanghai (CN)

(73) Assignee: L'OREAL, Paris (FR)

( * ) Notice: Subject to any disclaimer, the term of this patent is extended or adjusted under 35 U.S.C. 154(b) by 1120 days.

(21) Appl. No.: 17/291,754

(22) PCT Filed: Dec. 27, 2018

(86) PCT No.: PCT/CN2018/124204
§ 371 (c)(1),
(2) Date: May 6, 2021

(87) PCT Pub. No.: WO2020/133031
PCT Pub. Date: Jul. 2, 2020

(65) Prior Publication Data
US 2021/0386654 A1   Dec. 16, 2021

(51) Int. Cl.
| | |
|---|---|
| A61K 8/891 | (2006.01) |
| A61K 8/81 | (2006.01) |
| A61K 8/895 | (2006.01) |
| A61Q 1/06 | (2006.01) |

(52) U.S. Cl.
CPC ............ *A61K 8/891* (2013.01); *A61K 8/8111* (2013.01); *A61K 8/8182* (2013.01); *A61K 8/895* (2013.01); *A61Q 1/06* (2013.01); *A61K 2800/31* (2013.01); *A61K 2800/92* (2013.01)

(58) Field of Classification Search
CPC .... A61K 8/891; A61K 8/8111; A61K 8/8182; A61K 8/895; A61K 2800/31; A61K 2800/92; A61K 8/37; A61K 8/31; A61K 8/60; A61Q 1/06; A61Q 19/00
See application file for complete search history.

(56) References Cited

U.S. PATENT DOCUMENTS

| | | | |
|---|---|---|---|
| 6,423,322 B1 | 7/2002 | Fry | |
| 6,881,416 B2 * | 4/2005 | Fry | ........................ A61K 8/895 514/846 |
| 6,887,934 B2 | 5/2005 | Ferritto et al. | |
| 7,329,699 B2 | 2/2008 | Liew et al. | |
| 2003/0190301 A1 | 10/2003 | Fry | |
| 2008/0166309 A1 | 7/2008 | McDermott et al. | |
| 2008/0305062 A1 * | 12/2008 | Bui | ......................... A61Q 1/04 424/78.08 |
| 2012/0219516 A1 | 8/2012 | Ramada et al. | |
| 2015/0118171 A1 | 4/2015 | Arditty et al. | |
| 2015/0320673 A1 * | 11/2015 | Shimizu | ................... A61Q 1/06 514/772 |
| 2017/0349756 A1 | 12/2017 | Grüner et al. | |
| 2017/0360666 A1 | 12/2017 | Pottie et al. | |
| 2018/0214369 A1 | 8/2018 | Ebanks et al. | |

FOREIGN PATENT DOCUMENTS

| | | | |
|---|---|---|---|
| CN | 1275369 A | 12/2000 | |
| CN | 1739484 A | 3/2006 | |
| CN | 101322678 A | 12/2008 | |
| CN | 104321109 A | 1/2015 | |
| CN | 104379217 A | 2/2015 | |
| CN | 105451709 A | 3/2016 | |
| CN | 103025304 B | 6/2016 | |
| CN | 108721132 A | 11/2018 | |
| EP | 1 726 330 A2 | 11/2006 | |
| JP | 2000-355521 A | 12/2000 | |
| JP | 2008-189664 A | 8/2008 | |
| JP | 2015-520215 A | 7/2015 | |
| KR | 10-2015-0023844 A | 3/2015 | |
| RU | 2 147 221 C1 | 4/2000 | |
| RU | 2 651 045 C2 | 4/2018 | |
| RU | 2 672 915 C2 | 11/2018 | |
| WO | WO 2004/018563 A1 | 3/2004 | |
| WO | WO 2013/190136 A2 | 12/2013 | |
| WO | WO 2013/190703 A1 | 12/2013 | |
| WO | WO-2015014752 A1 * | 2/2015 | ............... A61K 8/31 |

(Continued)

OTHER PUBLICATIONS

"WO-2017057862-A1, Han, Machine Translation, 2017" (Year: 2017).*
Russian Office Action issued Mar. 7, 2023 in Russian Patent Application No. 2021109624/04, 13 pages.
Korean Office Action issued May 2, 2024 in Korean Patent Application No. 10-2021-7011536 (with English translation), 7 pages.
Anonymous, "Make-up and Skin-care Cosmetic Compositions Containing a Specific Silicon Resin Elastomer Gel", Research Disclosure, Kenneth Mason Publications, vol. 597, No. 55, Jan. 2014, pp. 1-10 (11 total pages), XP007142864.
"Innovation Zone 2015—Discover the lasts ingredients and the most innovative formulations", Internet Citation, Jan. 2015, pp. 1-49 (50 total pages), XP002749062, Retrieved from the Internet: URL:http://www.in-cosmetics.com/RXUK/RXUK_COS_EUROPE_INNOVATION_ZONE_GUIDE_2015_v16_LO.pdf?v=635666863387152785.

(Continued)

*Primary Examiner* — Margaret G Moore
(74) *Attorney, Agent, or Firm* — Oblon, McClelland, Maier & Neustadt, L.L.P.

(57) ABSTRACT

An anhydrous composition for caring for and/or making up keratin materials may include: (a) 10 to 40 wt. % of at least one non-volatile non-phenyl silicone oil, relative to the total weight of the composition; (b) at least one non-volatile hydrocarbon-based oil and/or phenyl silicone oil; (c) at least one high viscosity ester; and (d) reaction product of an unsaturated-functional silicone resin, an Si—H functional organopolysiloxane crosslinker bearing pendant hydrido functionality and optionally, an unsaturated hydrocarbon having four or more carbon atoms, in a low viscosity organopolysiloxane. A process for caring for and/or making up keratin materials, such as the skin and the lips, preferably the lips, make include applying such and anhydrous composition to the keratin materials.

20 Claims, No Drawings

(56) References Cited

FOREIGN PATENT DOCUMENTS

| WO | WO-2017057862 A1 * | 4/2017 | ............... A61K 8/19 |
| WO | WO-2017173270 A1 * | 10/2017 | ............... A61K 8/03 |

OTHER PUBLICATIONS

Extended European Search Report issued on Nov. 18, 2022 in European Patent Application No. 18944282.5, 16 pages.
Chinese Office Action and Search Report issued on Jan. 20, 2023 in Chinese Patent Application No. 201880099704.5 (with Translation of Category of Cited Documents), 10 pages.
Japanese Office Action issued on Jan. 4, 2023 in Japanese Patent Application No. 2021-527054 (with English translation), 8 pages.
International Search Report and Written Opinion issued on Oct. 9, 2019 in PCT/CN2018/124204 filed on Dec. 27, 2018.
Japanese Office Action issued Jun. 6, 2022 in Japanese Patent Application No. 2021-527054 (with English translation), 10 pages.
"A Novel Silicone Elastomer Gel Having Both High Film Formability / Sustainability and Smooth Feelings", Retrieved from the internet: http://www.aws-silicone.com/dems_media/other/Tech_library3.pdf, Sep. 15, 2013, 3 pages.
Russian Office Action issued Mar. 7, 2023 in Russian Patent Application No. 2021109624104 (previously filed; submitting English Translation only), 9 pages.
Russian Office Action and Search Report issued Apr. 28, 2022 in Russian Patent Application No. 2021109624/04(020697) (with English language translation), 17 pages.
Combined Chinese Office Action and Search Report issued Oct. 10, 2022 in Chinese Patent Application No. 201880099704.5 (with English translation of Category of Cited Documents), 11 pages.
Shiwen Ouyang, Intellectual Property Press, Apr. 30, 2017, pp. 176-177 (3 total pages).
Jiancal Du et al., CNKI, Dec. 31, 2011, 5 pages.
Russian Office Action issued Sep. 16, 2022 in Russian Patent Application No. 2021109624 (with English translation), 18 pages.
Korean Office Action issued Nov. 7, 2023 in Korean Patent Application No. 10-2021-7011536, 6 pages.

* cited by examiner

ANHYDROUS COMPOSITION FOR CARING FOR AND/OR MAKING UP KERATIN MATERIALS

CROSS-REFERENCE TO RELATED APPLICATIONS

The present application is the national stage of international application PCT/CN2018/124204, filed on Dec. 27, 2018, and claims the benefit thereof.

TECHNICAL FIELD

The present invention relates to an anhydrous composition for caring for and/or making up keratin materials such as the skin and the lips, preferably the lips. The present invention also relates to a process for caring for and/or making up keratin materials such as the skin and the lips, preferably the lips.

BACKGROUND

Compositions for caring for and/or making up the skin and/or the lips are produced to satisfy the need of moisturization or hydration of the skin and the lips.

Lipsticks with good moisturizing sensory, generally very easy to transfer to other surfaces such as hands, cups or clothing.

To date, some prior art documents relating to cosmetic compositions for making up and/or caring for the skin and/or the lips have been published.

WO 2013/191300 discloses a solid cosmetic composition for making up and/or caring for the skin and/or the lips, comprising in a physiologically acceptable medium at least one fatty phase comprising:
- from 5 to 30% by weight of (a) non-volatile hydrocarbonated apolar oils, or a mixture thereof, relative to the total weight of the composition.
- from 43 to 90% by weight of the total content of (a) non-volatile silicone oil(s) relative to the total weight of the composition, wherein at least one of said non-volatile silicone oil(s) is a non-volatile phenylated silicon oil, and
- from 3 to 30% by weight of (a) wax(es), or a mixture thereof, relative to the total weight of the composition.

WO 2012/165130 discloses a cosmetic for lips which is characterized by comprising: (a) 5 to 30 mass % of hydrogenerated polyisobutene; (b) 30 to 70 mass % of one or more kinds of methyl phenyl silicones separating when mixed with (a) at 25° C.; (c) 0.5 to 15 mass % of an oil separating when: mixed with (a) at 25° C.; and mixed with (b) at 25° C.; and (d) 4 to 12 mass % of a wax.

JP-A-2012-82188 discloses that a solid cosmetic for a lip comprises: (a) adhesion oil: (b) exudation oil, the viscosity of which is lower than that of the adhesion oil; and (c) wax dispersed at 90° C. and solidified at 25° C. when mixed at least with the exudation oil, and the solid cosmetic for a lip is separated when the (a) and the (b) are mixed at 25° C., and is characterized in that the (a) adhesion oil is dispersed into the (b) exudation oil or the (b) exudation oil is dispersed into the (a) adhesion oil.

In general, when women use makeup products, especially lip products such as lipstick or lip gloss, they hope that the colour of this product is not easily transferred after application and that the product results in good sensory, for example, non-sticky and non-dry feeling.

Thus, there is still a need to obtain products for caring for and/or making up keratin materials such as the skin and the lips which provide a deposit having good colour transfer resistance and a good sensory, for example, non-sticky and non-dry feeling.

SUMMARY OF THE INVENTION

One object of the present invention is thus to provide products for caring for and/or making up keratin materials such as the skin and the lips which provide a deposit having good colour transfer resistance and a good sensory, for example, non-sticky and non-dry feeling.

Another object of the present invention is to provide a process for caring for and/or making up keratin materials such as the skin and the lips, preferably the lips.

Thus, according to one aspect of the present invention, provided is an anhydrous composition for caring for and/or making up keratin materials comprising:
- a) 10%~40% by weight of at least one non-volatile non-phenyl silicone oil:
- b) at least one non-volatile hydrocarbon-based oil and/or phenyl silicone oil;
- c) at least one high viscosity ester; and
- d) reaction product of an unsaturated-functional silicone resin, an Si—H functional organopolysiloxane crosslinker bearing pendant hydrido functionality and optionally, an unsaturated hydrocarbon having four or more carbon atoms, in a low viscosity organopolysiloxane.

According to another aspect of the present invention, provided is a process for caring for and/or making up keratin materials such as the skin and the lips, preferably the lips, comprising applying the anhydrous composition as described above to the keratin materials.

It has been surprisingly found that upon application of the composition according to the present invention can achieve low color transfer is observed, meanwhile good sensory including non-sticky and non-dry feeling are obtained.

In addition, the anhydrous composition according to the present invention is easy to apply, i.e. it has good spreadability, and would not lapse in a container, i.e., it has good shape stability.

DETAILED DESCRIPTION OF THE INVENTION

The anhydrous composition for caring for and/or making up keratin materials according to the present invention comprises:
- a) 10%~40% by weight of at least one non-volatile non-phenyl silicone oil, relative to the total weight of the composition;
- b) at least one non-volatile hydrocarbon-based oil and/or phenyl silicone oil;
- c) at least one high viscosity ester; and
- d) reaction product of an unsaturated-functional silicone resin, an Si—H functional organopolysiloxane crosslinker bearing pendant hydrido functionality and optionally, an unsaturated hydrocarbon having four or more carbon atoms, in a low viscosity organopolysiloxane.

In some preferred embodiments, the anhydrous composition according to the present invention further comprises at least one wax and/or at least one colorant.

In some embodiments, the anhydrous composition according to the present invention is solid.

The term "solid" used herein means the hardness of the composition at 20° C. and at atmospheric pressure (760 mmHg) is greater than or equal to 30 Nm$^{-1}$ when it is measured according to the protocol described below.

The composition whose hardness is to be determined is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the present invention, expressed in Nm$^{-1}$, is measured using a DFGS2® tensile testing machine from the company Indelco-Chatillon.

The measurement is repeated three times and then averaged. The average of the three values read using the tensile testing machine mentioned above, noted Y, is given in grams. This average is converted into Newtons and then divided by L which represents the longest distance through which the wire passes. In the case of a cylindrical wand, L is equal to the diameter (in metres).

The hardness is converted into Nm$^{-1}$ by the equation below:

$(Y \times 10^{-3} \times 9.8)/L$.

For a measurement at a different temperature, the composition is stored for 24 hours at this new temperature before the measurement.

According to this measuring method, the composition according to the present invention preferably has hardness at 20° C. and at atmospheric pressure of greater than or equal to 40 Nm$^{-1}$ and preferably greater than 50 Nm$^{-1}$.

Preferably, the composition according to the present invention especially has a hardness at 20° C. of less than 500 Nm-1, especially less than 400 Nm$^{-1}$ and preferably less than 300 Nm$^{-1}$.

For the purposes of the present invention, the term "anhydrous" means that the composition according to the present invention contains less than 2% and preferably less than 0.5% by weight of water relative to the total weight of the composition. Where appropriate, such small amounts of water may be provided by ingredients of the composition that contain it in residual amount, but are not deliberately provided.

Preferably, the "keratin material" according to the present invention is the skin and the lips. By "skin", we intend to mean all the body skin, including the scalp. Still preferably, the keratin material is the lips.

Non-Volatile Non-Phenyl Silicone Oil(s)

The term "oil" means a water-immiscible non-aqueous compound that is liquid at room temperature (25° C.) and atmospheric pressure (760 mmHg).

The term "non-volatile" means an oil of which the vapour pressure at 25° C. and atmospheric pressure is non-zero and is less than 0.02 mmHg (2.66 Pa) and better still less than 10$^{-3}$ mmHg (0.13 Pa).

The term "silicone oil" means an oil containing at least one silicon atom, and in particular containing Si—O groups.

The term "non-phenyl silicone oil" denotes a silicone oil not bearing any phenyl substituents.

Representative examples of these non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

It should be noted that "dimethicone" (INCI name) corresponds to a polydimethylsiloxane (chemical name).

The non-volatile non-phenyl silicone oil is preferably chosen from non-volatile dimethicone oils.

In particular, these oils can be chosen from the following non-volatile oils:
polydimethylsiloxanes (PDMSs),
PDMSs comprising aliphatic groups, in particular alkyl or alkoxy groups, which are pendent and/or at the end of the silicone chain, these groups each comprising from 2 to 12 carbon atoms.
PDMSs comprising aliphatic groups, or functional groups such as hydroxyl, thiol and/or amine groups,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{12}$ alkyl groups, and/or functional groups such as hydroxyl, thiol and/or amine groups.

The non-phenyl silicone oil may be chosen in particular from silicones of formula (I):

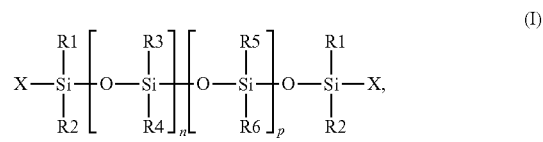

in which:
$R_1$, $R_2$, $R_5$, and $R_6$ are, together or separately, an alkyl radical containing from 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical.
n and p are integers chosen so as to have a fluid compound, in particular of which the viscosity at 25° C. is between 100 centistokes (cSt) and 1,000 cSt.

As non-volatile non-phenyl silicone oils which can be used according to the present invention, mention may be made of those for which:
the substituents $R_1$ to $R_6$ and X represent a methyl group, and p and n are such that the viscosity is 100 cSt or 350 cSt, for example the products sold respectively under the names Belsil DM100® formulation and Dow Corning 200 Fluid 350 CS® formulation by the company Dow Corning;
the substituents $R_1$ to $R_6$ represent a methyl group, the group X represents a hydroxyl group, and n and p are such that the viscosity is 700 cSt, for example the product sold under the name Baysilone Fluid T0.7® formulation by the company Momentive:
the substituents $R_1$ to $R_6$ represent a methyl group, the group X represents a hydroxyl group, and n and p are such that the viscosity is 1,000 cSt.

The non-volatile non-phenyl silicone oil(s) can be present in an amount ranging from 10% to 40% by weight, preferably 15% to 35% by weight, more preferably, 18% to 30% by weight, relative to the total weight of the composition.

Non-Volatile Hydrocarbon-Based Oil(s) and/or Phenyl Silicone Oil(s)

Non-Volatile Hydrocarbon-Based Oil(s)

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

These oils may be of plant, mineral or synthetic origin.

Preferably, the non-volatile hydrocarbon-based oil may be chosen from linear or branched hydrocarbons of mineral or synthetic origin, such as:

liquid paraffin or derivatives thereof,
squalane,
isoeicosane,
naphthalene oil,
polybutylenes, for instance Indopol H-100® formulation (molar mass or MW=965 g/mol), Indopol H-300® formulation (MW=1340 g/mol) and Indopol H-1500® formulation (MW=2160 g/mol) sold or manufactured by the company Amoco,
hydrogenated or non-hydrogenated polyisobutenes, such as for example Parleam® formulation sold by the company Nippon Oil Fats, Panalane H-300 E® formulation sold or manufactured by the company Amoco (MW=1340 g/mol), Viseal 20000® formulation sold or manufactured by the company Synteal (MW=6,000 g/mol) and Rewopal PIB 1000® formulation sold or manufactured by the company Witco (MW=1,000 g/mol), or alternatively Parleam Lite® formulation sold by NOF Corporation,
decene/butene copolymers, polybutene/polyisobutene copolymers, in particular Indopol L-14,
hydrogenated and non-hydrogenated polydecenes, for instance Puresyn 10® formulation (MW=723 g/mol) and Puresyn 150R® formulation (MW=9,200 g/mol) sold or manufactured by the company Mobil Chemicals, or alternatively Puresyn 6® formulation sold by ExxonMobil Chemical,
synthetic esters, for instance the oils of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 16$, for instance purcellin oil (cetostearyl octanoate), isononyl isononanoate, $C_{12}$ to $C_{15}$ alkyl benzoate, 2-ethylhexyl palmitate, octyldodecyl neopentanoate, stearyl heptanoate, stearyl caprylate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate; preferably, the preferred synthetic esters $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms are such that $R_1$ and $R_2 \geq 20$:
copolymers of vinylpyrrolidone, such as: vinylpyrrolidone/1-hexadecene copolymer, for example Antaron V-216® formulation marketed or produced by ISP (MW=7300 g/mol),
and mixtures thereof.

Preferably, the composition according to the present invention comprises at least one non-volatile hydrocarbon-based oil chosen from polybutenes, polyisobutenes, hydrogenated polyisobutenes, poly decenes and/or hydrogenated polydecenes, copolymers of vinylpyrrolidone and mixtures thereof.

According to one preferred embodiment, a composition according to the present invention comprises at least one non-volatile hydrocarbon-based oil chosen from hydrogenated polyisobutylene, hydrogenated polydecene and copolymers of vinylpyrrolidone.

According to one preferred embodiment, a composition according to the present invention comprises at least one non-volatile hydrocarbon-based oil chosen from synthetic esters, for instance purcellin oil (cetostearyl octanoate), isononyl isononanoate, $C_{12}$ to $C_{15}$ alkyl benzoate, 2-ethylhexyl palmitate, octyldodecyl neopentanoate, stearyl heptanoate, stearyl caprylate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexvldecyl laurate, 2-octyldecyl palmitate, 2-octyldodecyl myristate, 2-diethvlhexvl succinate and copolymers of vinylpyrrolidone, for example, vinylpvrrolidone/1-hexadecene copolymer.

According to one preferred embodiment, a composition according to the present invention comprises at least one non-volatile hydrocarbon-based oil chosen from hydrogenated polyisobutenes, octyldodecyl neopentanoate, stearyl heptanoate, stearyl caprylate, vinylpyrrolidone/1-hexadecene copolymer and a mixture thereof.

The inventors have discovered unexpectedly that the composition comprising vinylpyrrolidone/1-hexadecene copolymer has good shininess.

Non-Volatile Phenyl Silicone Oils

The expression "phenyl silicone oil" denotes a silicone oil bearing at least one phenyl substituent.

These non-volatile phenyl silicone oils may be chosen from those also having at least one dimethicone fragment, or from those not having one.

According to the present invention, a dimethicone fragment corresponds to the following unit:

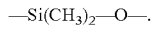

$-Si(CH_3)_2-O-$.

The non-volatile phenyl silicone oil may thus be chosen from:

a) Phenyl Silicone Oils Optionally Having a Dimethicone Fragment Corresponding to Formula (II) Below:

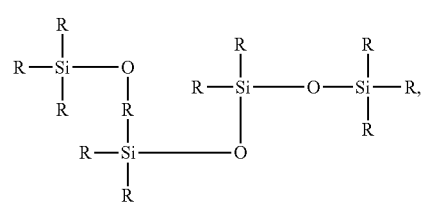

(II)

in which the groups R, which are monovalent or divalent, represent, independently of each other, a methyl or a phenyl, with the proviso that at least one group R represents a phenyl.

Preferably, in this formula, the phenyl silicone oil comprises at least three, for example at least four, at least five or at least six, phenyl groups.

b) Phenyl Silicone Oils Optionally Having a Dimethicone Fragment Corresponding to Formula (III) Below:

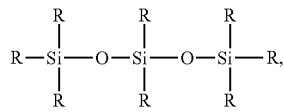
(III)

in which the groups R represent, independently of each other, a methyl or a phenyl, with the proviso that at least one group R represents a phenyl.

Preferably, in this formula, the compound of formula (III) comprises at least three, for example at least four or at least five, phenyl groups.

Mixtures of different phenylorganopolysiloxane compounds described above can be used.

Examples that may be mentioned include mixtures of triphenyl-, tetraphenyl-, or pentaphenyl-organopolysiloxanes.

Among the compounds of formula (III), mention may be made more particularly of phenyl silicone oils not having any dimethicone fragments, corresponding to formula (III) in which at least 4 or at least 5 radicals R represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI® formulation or Dow Corning 555® Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554® Cosmetic Fluid by Dow Corning can also be used.

They correspond in particular to formulae (IV) and (IV') below:

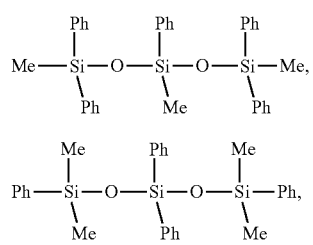

c) Phenyl Silicone Oils Having at Least One Dimethicone Fragment Corresponding to Formula (V) Below:

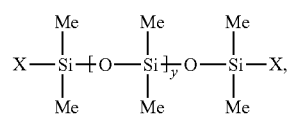
(V)

in which Me represents methyl, y is between 1 and 1,000, and X represents —$CH_2$—$CH(CH_3)(Ph)$.

d) Phenyl Silicone Oils Corresponding to Formula (VI) Below, and Mixtures Thereof:

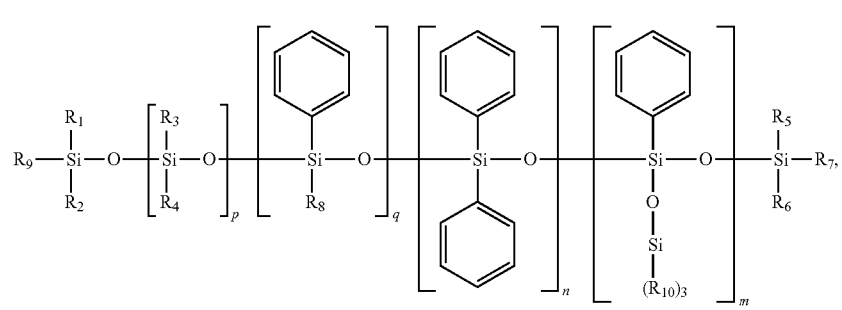
(VI)

in which:

$R_1$ to $R_{10}$, independently of each other, are saturated or unsaturated, linear, cyclic or branched $C_1$-$C_3$, hydrocarbon-based radicals, m, n, p, and q are, independently of each other, integers between 0 and 900, with the proviso that the sum m+n+q is other than 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$, hydrocarbon-based radical, or a monocyclic or polycyclic $C_6$-$C_{14}$, and in particular $C_{10}$-$C_{13}$, aryl radical, or an aralkyl radical, the alkyl part of which is preferably $C_1$-$C_3$ alkyl.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical, and in addition may be a methyl radical.

According to a more particular embodiment of formula (VI), mention may be made of:

i) Phenyl Silicone Oils Optionally Having at Least One Dimethicone Fragment Corresponding to Formula (VII) Below, and Mixtures Thereof:

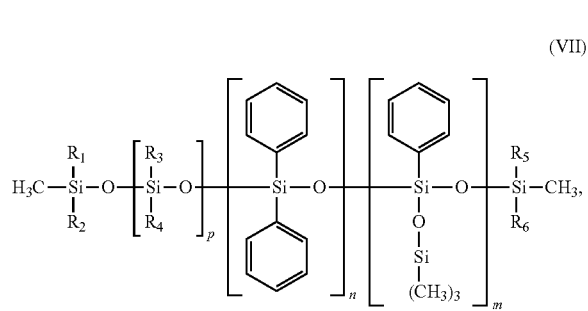

(VII)

in which:
- $R_1$ to $R_6$, independently of each other, are saturated or unsaturated, linear, cyclic or branched $C_1$-$C_{30}$ hydrocarbon-based radicals, a preferably $C_6$-$C_{14}$ aryl radical or an aralkyl radical, the alkyl part of which is $C_1$-$C_3$ alkyl,
- m, n, and p are, independently of each other, integers between 0 and 100, with the proviso that the sum n+m is between 1 and 100.

Preferably, $R_1$ to $R_6$, independently of each other, represent a $C_1$-$C_{20}$, in particular $C_1$-$C_{18}$, hydrocarbon-based, preferably alkyl, radical, or a $C_6$-$C_{14}$ aryl radical which is monocyclic (preferably $C_6$) or polycyclic and in particular $C_{10}$-$C_{13}$, or an aralkyl radical (preferably the aryl part is $C_6$ aryl; the alkyl part is $C_1$-$C_3$ alkyl).

Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical, and in addition may be a methyl radical. Preferably, m=1 or 2 or 3, and/or n=0 and/or p=0 or 1 can be applied, in formula (VII).

According to one particular embodiment, the non-volatile phenyl silicone oil is chosen from phenyl silicone oils having at least one dimethicone fragment.

Preferably, such oils correspond to compounds of formula (VII) in which:
A) m=0 and n and p are. Independently of Each Other. Integers Between 1 and 100

Preferably, $R_1$ to $R_6$ are methyl radicals.

According to this embodiment, the silicone oil is preferably chosen from a diphenyl dimethicone such as KF-54® formulation from Shin Etsu (400 cSt), KF54HV® formulation from Shin Etsu (5,000 cSt), KF-50-300CS® formulation from Shin Etsu (300 cSt), KF-53® formulation from Shin Etsu (175 cSt) or KF-50-100CS® formulation from Shin Etsu (100 cSt).

B) p is Between 1 and 100, the Sum n+m is Between 1 and 100, and n=0

These phenyl silicone oils optionally having at least one dimethicone fragment correspond more particularly to formula (VIII) below:

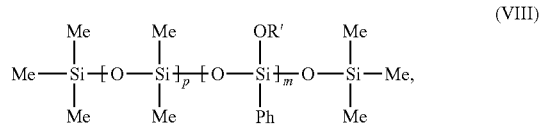

(VIII)

in which Me is methyl and Ph is phenyl, OR' represents a group —$OSiMe_3$, and p is 0 or is between 1 and 1,000, and m is between 1 and 1,000. In particular, m and p are such that the compound (VIII) is a non-volatile oil.

According to an embodiment of the present invention, non-volatile phenyl silicone having at least one dimethicone fragment, p is between 1 and 1,000 and m is more particularly such that the compound (VIII) is a non-volatile oil. Trimethylsiloxyphenyl dimethicone, sold in particular under the reference Belsil PDM 1,000 by the company Wacker, may, for example, be used.

According to an embodiment of non-volatile phenyl silicone not having a dimethicone fragment, p is equal to 0 and m is between 1 and 1,000, and in particular is such that the compound (VIII) is a non-volatile oil.

Phenyltrimethylsiloxytrisiloxane, sold in particular under the reference Dow Corning 556® Cosmetic Grade Fluid (DC556), may, for example, be used.

ii) Non-Volatile Phenyl Silicone Oils not Having a Dimethicone Fragment Corresponding to Formula (IX) Below, and Mixtures Thereof:

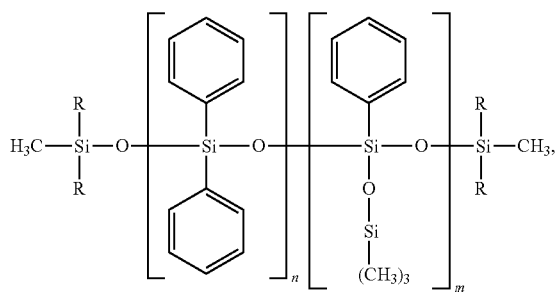

(IX)

in which:
- R, independently of each other, are saturated or unsaturated, linear, cyclic or branched $C_1$-$C_{30}$ hydrocarbon-based radicals, preferably R is a $C_1$-$C_{30}$ alkyl radical, a preferably $C_6$-$C_{14}$ aryl radical, or an aralkyl radical, the alkyl part of which is $C_1$-$C_3$ alkyl,
- m and n are, independently of each other, integers between 0 and 100, with the proviso that the sum n+m is between 1 and 100.

Preferably, R, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$ and more particularly $C_4$-$C_{10}$, hydrocarbon-based radical, a monocyclic or polycyclic $C_6$-$C_{14}$, and in particular $C_{10}$-$C_{13}$, aryl radical, or an aralkyl radical of which preferably the aryl part is $C_6$ aryl and the alkyl part is $C_1$-$C_3$ alkyl.

Preferably, the groups R may each represent a methyl, ethyl, propyl, butyl, isopropyl, decyl, dodecyl or octadecyl radical, or alternatively a phenyl, tolyl, benzyl or phenethyl radical.

The groups R may in particular be identical, and in addition may be a methyl radical.

Preferably, m=1 or 2 or 3, and/or n=0 and/or p=0 or 1 can be applied, in formula (IX).

According to one preferred embodiment, n is an integer between 0 and 100 and m is an integer between 1 and 100, with the proviso that the sum n+m is between 1 and 100, in formula (IX). Preferably, R is a methyl radical.

According to one embodiment, a phenyl silicone oil of formula (IX) with a viscosity at 25° C. of between 5 and 1500 mm²/s (i.e. 5 to 1500 cSt), and preferably with a viscosity of between 5 and 1,000 mm²/s (i.e. 5 to 1,000 cSt), may be used.

According to this embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A1, formulation from Shin Etsu, or the Silbione 70663V30® oil from Rhone-Poulenc (28 cSt). The values in parentheses represent the viscosities at 25° C.

e) Phenyl Silicone Oils Optionally Having at Least One Dimethicone Fragment Corresponding to the Following Formula, and Mixtures Thereof:

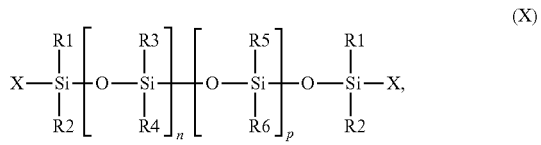

(X)

in which:
$R_1$, $R_2$, $R_5$, and $R_6$, which may be identical or different, are an alkyl radical containing 1 to 6 carbon atoms,
$R_3$ and $R_4$, which may be identical or different, are an alkyl radical containing from 1 to 6 carbon atoms or an aryl radical (preferably $C_6$-$C_{14}$), with the proviso that at least one of $R_3$ and $R_4$ is a phenyl radical,
X is an alkyl radical containing from 1 to 6 carbon atoms, a hydroxyl radical or a vinyl radical,
n and p being an integer greater than or equal to 1, chosen so as to give the oil a weight-average molecular weight of less than 200,000 g/mol, preferably less than 150,000 g/mol, and more preferably less than 100,000 g/mol.

f) and a mixture thereof.

According to one preferred embodiment, the composition according to the present invention comprises both a non-volatile hydrocarbon-based oil and a non-volatile phenyl silicone oil.

According to one more preferred embodiment, the composition according to the present invention comprises both a non-volatile hydrocarbon-based oil chosen from hydrogenated polyisobutenes, octyldodecyl neopentanoate, stearyl heptanoate, stearyl caprylate, vinylpyrrolidone/I-hexadecene copolymer and mixtures thereof, and a non-volatile phenyl silicone oil chosen from phenyl silicone oils not having any dimethicone fragments, corresponding to formula (II) in which at least 4 or at least 5 radicals R represent a phenyl radical, the remaining radicals representing methyls, i.e phenyl silicone oils not having a dimethicone fragment corresponding to formula (III) below:

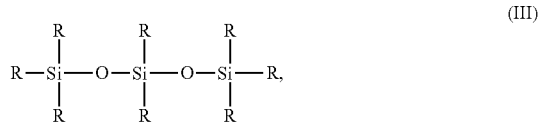

(III)

wherein at least 3, at least 4 or at least 5 radicals R represent a phenyl radical, the remaining radical R represent methyls,
more preferably trimethylpentaphenyltrisiloxane or tetramethyltetraphenyltrisiloxane.

The non-volatile hydrocarbon-based oil(s) and/or phenyl silicone oil(s) are present in a total content ranging from 30% to 70% by weight, preferably from 35% to 65% by weight and more preferably from 40% to 60% by weight relative to the total weight of the composition.

High Viscosity Esters

By high viscosity, it is meant that the ester has a viscosity of at least 10,000 cps at room temperature.

Preferred examples of such esters include, but are not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio: the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are $C_{18}$ mono- and/or di-unsaturated and behenic, in a molar ratio of unsaturates: behenic of 1:7 to 3:5. In another embodiment, the sugar polyester is the octaester of sucrose in which there are about 7 behenic fatty acid moieties and about 1 oleic acid moiety in the molecule. Other materials may include cottonseed oil or soybean oil fatty acid esters of sucrose.

A preferred high viscosity ester for use in the present invention is chosen from $C_2$-$C_6$ carboxylic acid ester of sucrose. More particularly, the $C_2$-$C_6$ carboxylic acid ester of sucrose is chosen from mixed esters of acetic acid, isobutyric acid and sucrose, and in particular sucrose diacetate hexakis(2-methylpropanoate), such as the product sold under the name Sustane SAIB Food Grade Kosher by the company Eastman Chemical (INCI name: sucrose acetate isobutyrate), which has a viscosity of about 100,000 cps at 30° C. and a refractive index of about 1.5 at 20° C.

The at least one high viscosity ester is advantageously present in the composition of the present invention in an amount of from 1% to 20% by weight, preferably from 3% to 15% by weight, and more preferably from 4% to 10% by weight, relative to the total weight of the composition.

Reaction Product of an Unsaturated-Functional Silicone Resin, an Si—H Functional Organopolysiloxane Crosslinker Bearing Pendant Hydrido Functionality and Optionally, an Unsaturated Hydrocarbon Having Four or More Carbon Atoms, in a Low Viscosity Organopolysiloxane The composition according to the present invention comprises reaction product of an unsaturated-functional silicone resin, an Si—H functional organopolysiloxane crosslinker bearing pendant hydrido functionality and optionally, an unsaturated hydrocarbon having four or more carbon atoms, in a low viscosity organopolysiloxane.

The reaction is a hydrosilylation reaction which takes place in conjunction with a hydrosilylation catalyst, preferably a platinum-containing catalyst.

The low viscosity organopolysiloxane comprises minimally 20 weight percent of the overall reaction system, preferably minimally 50 weight percent, more preferably 60 weight percent or more, and most preferably in the range of 65 to 90 weight percent.

The low viscosity and preferably volatile organopolysiloxane may be a low molecular weight oligomeric polydialkylsiloxane, or a cyclic siloxane. Most preferably, the low viscosity organopolysiloxane is an oligomeric polydimethylsiloxane or a cyclic polydimethylsiloxane. Other alkyl, aryl, alkaryl, and aralkyl groups are also acceptable, of course, for example, phenyl groups, benzyl groups. $C_2$-$C_{18}$ alkyl groups, and the like. However, because of cost considerations and the ease of formulation, organopolysiloxanes with methyl groups attached to the silicon atoms are highly preferred. Most preferably, the organopolysiloxanes are linear trimethylsilyl terminated polydimethylsiloxanes having on average from 2 to 50 silicon atoms in the organopolysiloxane backbone inclusive of the trimethylsilyl end groups. If volatility is desired, the number of silicon atoms should be greatly restricted, for example, to below 10, and preferably below 6.

Preferably, the organopolysiloxanes are volatile organopolysiloxanes. As indicated previously, volatility can be achieved in linear organopolysiloxanes by selection of oligomeric organopolysiloxanes with at most about 6 to 10 silicon atoms in the organopolysiloxane backbone. Preferably, however, cyclic organopolysiloxanes having from 3 to 6 silicon atoms are utilized, for example, hexamethylcyclotrisiloxane, octamethylcyclotetrasiloxane, decamethylcyclopentasiloxane, dodecamethylcyclohexasiloxane, and the like. As with the linear organopolysiloxanes, groups other than methyl groups may be present, for example, $C_2$-$C_{18}$ alkyl groups, preferably $C_{2-4}$ alkyl groups, aryl groups, and the like.

Preferably, said low viscosity organopolysiloxane is a linear or branched organopolysiloxane having from 2 to about 10 silicon atoms, or a cyclic organopolysiloxane having from 3 to about 6 silicon atoms. Preferably, the repeating siloxane moieties of said low viscosity organopolysiloxane comprise dimethylsiloxy groups.

The unsaturated organopolysiloxane resin is a vinyl functional MQ resin or similar, highly crosslinked resin containing M, Q, and/or T moieties, and optionally a minor amount of D moieties. Such resins are by now well-known in the art. The term M refers to monofunctional units while the term Q refers to tetrafunctional units. In other words, an MQ resin contains predominantly M units wherein silicon is attached to only one oxygen in the cross-linked molecules, and $SiO_{4/2}$ Q units wherein each silicon atom is attached to four other oxygen atoms, resulting in a high level of cross-linking. In many MQ resins, small amounts of difunctional $R_2SiO_{2/2}$ and trifunctional $RSiO_{3/2}$ (D and T units, respectfully), are also present. MQ resins are frequently produced by the hydrolysis of silanes such as tetraethoxysilane, vinyldimethylethoxysilane and trimethylethoxysilane. The resulting MQ resin frequently retains some residual alkoxy functionality as a result of the method of its preparation, and will occasionally include other functionalities such as silanol functionality as well. A preferred MQ resin is MQ resin 804, available from Wacker Silicones Corporation, Adrian, Mich., which contains approximately 1.8 weight percent vinyl functionality. MQ resins having unsaturation other than vinyl, including vinyloxy, allyl, allyloxy, propenyl, etc., are less commonly available, but may be used also. The term "resin" is used herein in its customary meaning, i.e. a highly three-dimensionally crosslinked polymer containing a majority of M units, and T and/or Q units. MT, MQ, and MQT resins are thus preferred.

The unsaturated silicone resins can contain a variety of hydrosilatable unsaturated groups, including both ethylenic and ethylynic unsaturation. It is preferable, although not mandatory, that the unsaturation be terminal. For example, in hexenyl unsaturated groups, terminal (ω) hexenyl groups are preferred. The unsaturated groups may also be unsaturated ether groups such as vinyl ether groups, and may be other heteroatom containing groups as well, i.e. (meth)acryloxy groups. Vinyl and allyl groups are most preferable, as these are commercially more easily obtainable at reasonable cost. However, groups such as ω-hexenyl or ω-octenyl may allow preparation of products with unusual property profiles and uses.

Preferably, said unsaturated organopolysiloxane resin is a vinyl-functional MQ resin.

The Si—H functional organopolysiloxane is used as a cross-linking agent. It may or may not in addition to these Si—H functional units, also include terminal Si—H units. A preferred crosslinker is EL Crosslinker 525, a poly(methylhydrogen)dimethylsiloxane containing approximately 0.54 weight percent silicon-bonded hydrogen atoms and having a weight average molecular weight of ca. 29,100 Daltons, measured with a 2-column SEC, refractive index detector, calibrated with polystyrene. The weight average molecular weight of the crosslinker may vary from about 134 Da to preferably 40,000 Da or higher, preferably from 5000 Da to 40,000 Da, and more preferably from 10,000 Da to 35,000 Da. The crosslinkers must contain minimally 3 Si—H bound hydrogens, and preferably contain in excess of 5 Si—H bound hydrogens per molecule, more preferably 10 or more, and most preferably 20 or more.

By the term "pendant hydrido functionality" is meant organopolysiloxanes where at least a portion of the total Si—H functionality is located along the polymer backbone, i.e., in groups such as methylhydrogensiloxy or ethylhydrogensiloxy groups. Terminal Si—H functionality may also be present, so long as pendant hydrido functionality is present as well. It is possible to employ an Si—H functional organopolysiloxanes having only terminal unsaturation, such as dimethylhydrogensiloxy-end capped polydimethylsiloxanes. The useable proportions of such terminal Si—H functional siloxanes is inversely proportional to molecular weight, with larger amounts of αω—Si—H functional $Si_2$, $Si_3$, and $Si_4$ di- and oligosiloxanes being useful as compared to higher molecular weight αω—Si—H functional organopolysiloxanes.

For reasons of cost, it is preferable that the majority of Si-bound hydrocarbon groups in the Si—H functional cross-linkers be methyl, ethyl, or phenyl groups, preferably methyl or ethyl groups, and most preferably methyl groups. However, other higher molecular weight groups such as isooctyl, nonylphenyl, and the like are also useful The Si—H functional crosslinkers may also contain alkoxy groups, particularly less reactive higher alkoxy groups such as octyloxy or isooctyloxy groups. While lower alkoxy groups such as methoxy or ethoxy groups are relatively reactive, higher alkyl alkoxy groups are generally far less reactive, many of these being stable in the presence of water for extended periods of time.

Preferably, said Si—H functional organopolysiloxane is a poly(methylhydrogen)dimethyl siloxane.

The unsaturated hydrocarbon component is a hydrosilylatable hydrocarbon with at least 4 carbon atoms, preferably at least 6 carbon atoms, more preferably at least 8 carbon atoms, and most preferably at least 10 carbon atoms. While there is no fixed upper limit to the number of carbon atoms, it is preferable that the unsaturated hydrocarbon component contain less than 30 carbon atoms, preferably less than 24 carbon atoms. Preferably, the unsaturated hydrocarbon contains between 10 carbon atoms and 24 carbon atoms, more preferably between 12 and 20 carbon atoms.

The unsaturated hydrocarbon component may be straight chain, branched, or cyclic. Examples include, but are not limited to, 1-butene, 1-pentene, 2-butene, 2-pentene, 1-hexene, 2-hexene, 3-hexene, 1-octene, isooctene, 1-decene, 1-dodecene, cyclohexene, methylcyclohexene, hexylcyclohexene, norbornene, camphene, etc. Where the unsaturated hydrocarbon moiety contains greater than 6 carbon atoms, the moiety may contain one or more heteroatoms interspersed along the backbone. i.e., 1-butenyloxybutane, vinyloxyhexane, and the like. In addition, when the hydrocarbon moiety contains in excess of 8 carbon atoms, it may contain a carboxylic acid or ester group, for example linolenic acid or linolenic acid methyl ester, a carboxylic acid amide group, or other polar group. The hydrocarbon moiety must be essentially oleophilic, i.e., preferably has an HLB of less than 4, preferably less than 2 when hydrophilic or polar groups are present. The ratio of carbon atoms in the unsaturated hydrocarbon component to heteroatoms O, N, or S must be at least 4:1, and more preferably 6:1 or more.

The ratio of moles of unsaturation in the resin to moles of Si—H is preferably in the range of 0.07 to 0.74, more preferably 0.07 to 0.34, and most preferably 0.07 to 0.23. Ratios of 0.13 have proven quite satisfactory when MQ resins are employed. The ratio of moles of hydrocarbon unsaturation to moles of Si—H is preferably in the range of 0.04 to 1.82, more preferably 0.04 to 0.66, and most preferably about 0.29.

The ratio of moles of unsaturation in the MQ resin to moles of Si—H is preferably in the range of 0.2 to 1.5, more preferably 0.3 to 1.2, and most preferably 0.4 to 0.9. Ratios of 0.85 to 0.88 have proven quite satisfactory.

In some embodiments, the composition according to the present invention comprises the reaction product of an unsaturated-functional silicone resin and an Si—H functional organopolysiloxane crosslinker bearing pendant hydrido functionality in a low viscosity organopolysiloxane, said low viscosity organopolysiloxane is present in an amount of 75% to 90%; said unsaturated organopolysiloxane is present in an amount of about 5% to about 25%, and said Si—H functional organopolysiloxane is present in an amount of about 1-8%, based on the total weight of the reaction system.

Preferably, said low viscosity organopolysiloxane is present in an amount of 80% to 90%; said unsaturated organopolysiloxane is present in an amount of about 10% to about 20%, and said Si—H functional crosslinker is present in an amount of about 1-5%, based on the total weight of the reaction system.

The reaction product of an unsaturated-functional silicone resin and an Si—H functional organopolysiloxane crosslinker bearing pendant hydrido functionality in a low viscosity organopolysiloxane can be obtained by the process described, for example, in U.S. Pat. No. 6,423,322.

According to one preferred embodiment, a reaction product of vinyl MQ resin and poly(methylhydrogen)dimethyl siloxane in dimethicone is used in the composition according to the present invention.

In particular, use may be made of DIMETHICONE (and) DIMETHICONE/VINYLTRIMETHYLSILOXYSILICATE CROSSPOLYMER® formulation from Wacker Silicones Corporation.

In some embodiments, the composition according to the present invention comprises the reaction product of an unsaturated-functional silicone resin and an Si—H functional organopolysiloxane crosslinker bearing pendant hydrido functionality and an unsaturated hydrocarbon having four or more carbon atoms in a low viscosity organopolysiloxane.

The reaction product of an unsaturated-functional silicone resin and an Si—H functional organopolysiloxane crosslinker bearing pendant hydrido functionality and an unsaturated hydrocarbon having four or more carbon atoms in a low viscosity organopolysiloxane can be obtained by the process described, for example, in U.S. Pat. No. 6,881,416.

According to one embodiment, a reaction product of vinyl MQ resin, and poly(methylhydrogen)dimethylsiloxane and $C_{10}$-$C_{24}$ unsaturated linear or branched alkene in dimethicone is used in the composition according to the present invention.

In particular, use may be made of ISODODECAN (and) VINYLDIMETHYUTRIMETHYLSILOXYSILICATE STEARYL DIMETHICONE CROSSPOLYMER® formulation from Wacker Silicones Corporation.

Preferably, the reaction product of an unsaturated-functional silicone resin, an Si—H functional organopolysiloxane crosslinker bearing pendant hydrido functionality and optionally, an unsaturated hydrocarbon having four or more carbon atoms, in a low viscosity organopolysiloxane is present in amount ranging from 0.5% to 20% by weight, preferably from 1% to 15% by weight and more preferably from 1% to 10% by weight relative to the total weight of the composition.

Wax(s)

The wax under consideration in the context of the present invention is generally a lipophilic compound that is solid at room temperature (25° C.), with a solid/liquid reversible change of state, having a melting point of greater than or equal to 30° C., preferably greater than or equal to 40° C., which may be up to 200° C. and in particular up to 120° C.

Waxes used in the present invention includes waxes of animal origin, waxes of plant origin, waxes of mineral origin, synthetic waxes, and various fractions of waxes of natural origin.

Animal waxes include, but are not limited to, beeswax, spermaceti, lanolin wax, derivatives of lanoline and China insect waxes. Vegetable waxes includes, but are not limited to, rice wax, carnauba wax, candelilla wax, ouricurry wax, cork fiber wax, sugar cane wax, cocoa butter, Japan wax and sumac wax. Mineral waxes include, but are not limited to, montan wax, microcrystalline waxes, paraffins, ozokerite, petroleum jelly and ceresine. Synthetic waxes include, but are not limited to, polyethylene homopolymer and copolymer waxes, synthetic beewax, waxes obtained by the Fisher and Tropsch synthesis, and silicon waxes.

Waxes obtained by catalytic hydrogenation of animal or vegetable oils, having linear or branched $C_8$-$C_{32}$ fatty chains are also used, as well as fatty esters and glycerides.

Waxes also include silicone waxes, among which, mention may be made of polymethylsiloxane alkyls, alkoxys and/or esters. The waxes may be in the form of stable dispersions of colloidal wax particles, in according with known methods, such as "Microemulsions Theory and Practice", L. M. Prince Ed., Academic Press (1977), pages 21-32. Lignate wax may also be used.

Waxes useful in the composition according to the present invention may provide one or more of the following properties, including, but not limited to, bulking, texture, and a degree of water resistance. The waxes should not substantially reduce the gloss properties of a glossy film former, if presents.

According to a particularly preferred embodiment, the wax(es) used in the present invention is chosen from synthetic wax, paraffin, microcrystalline wax, or mixtures thereof.

The wax(es) can be present in an amount ranging from 5% to 30% by weight, preferably 7% to 20% by weight, more preferably 8% to 15% by weight, relative to the total weight of the composition.

Colorant(s)

For the purposes of the present invention, the term "colorant" means a compound that is capable of producing a colored optical effect when it is formulated in sufficient amount in a suitable cosmetic medium.

The colorant under consideration in the context of the present invention may be chosen from water-soluble or water-insoluble, liposoluble or non-liposoluble, organic or inorganic colorants, and materials with an optical effect, and mixtures thereof.

Water-Soluble Dyes

The water-soluble colorants used according to the present invention are more particularly water-soluble dyes.

For the purposes of the present invention, the term "water-soluble dye" means any natural or synthetic, generally organic compound which is soluble in an aqueous phase or water-miscible solvents and which is capable of imparting colour. In particular, the term "water-soluble" is intended to characterize the capacity of a compound to dissolve in water, measured at 25° C., to a concentration at least equal to 0.1 g/l (production of a macroscopically isotropic, transparent, colored or colorless solution). This solubility is in particular greater than or equal to 1 g/l.

As water-soluble dyes that are suitable for use in the present invention, mention may be made in particular of synthetic or natural water-soluble dyes, for instance FD&C Red 4 (CI: 14700), DC Red 6 (Lithol Rubine Na; CI: 15850), DC Red 22 (CI: 45380), DC Red 28 (CI: 45410 Na salt), DC Red 30 (CI: 73360). DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570). FDC Blue 1 (CI: 42090).

As non-limiting illustrations of sources of water-soluble colorant(s) that may be used in the context of the present invention, mention may be made in particular of those of natural origin, such as extracts of cochineal carmine, of beetroot, of grape, of carrot, of tomato, of annatto, of paprika, of henna, of caramel and of curcumin.

Thus, the water-soluble colorants that are suitable for use in the present invention are in particular carminic acid, betanin, anthocvans, enocyanins, lycopene, β-carotene, bixin, norbixin, capsanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble colorants are in particular approved for food use. Representatives of these dyes that may be mentioned more particularly include dyes of the carotenoid family, referenced under the food codes E120, E162, E163, E160a-g, E150a, E101, E100, E140 and E141.

Pigments

The term "pigments" should be understood as meaning white or coloured, inorganic (mineral) or organic particles, which are insoluble in a liquid organic phase, and which are intended to color and/or opacify the composition and/or the deposit produced with the composition.

The pigments may be chosen from mineral pigments, organic pigments and composite pigments (i.e., pigments based on mineral and/or organic materials).

The pigments may be chosen from monochromatic pigments, lakes and pigments with an optical effect, for instance goniochromatic pigments and nacres.

The mineral pigments may be chosen from metal oxide pigments, chromium oxides, iron oxides (black, yellow, red), titanium dioxide, zinc oxides, cerium oxides, zirconium oxides, chromium hydrate, manganese violet, Prussian blue, ultramarine blue, ferric blue, metal powders such as aluminum powders and copper powder, and mixtures thereof.

Organic lakes are organic pigments formed from a dye attached to a substrate.

The lakes, which are also known as organic pigments, may be chosen from the materials below, and mixtures thereof:
  cochineal carmine,
  organic pigments of azo dyes, anthraquinone dyes, indigoid dyes, xanthene dyes, pyrene dyes, quinoline dyes, triphenylmethane dyes or fluorane dyes.

Among the organic pigments that may in particular be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5. FD&C Yellow No. 6;
  the organic lakes may be insoluble sodium, potassium, calcium, barium, aluminium, zirconium, strontium or titanium salts of acidic dyes such as azo, anthraquinone, indigoid, xanthene, pyrene, quinoline, triphenylmethane or fluorane dyes, these dyes possibly comprising at least one carboxylic or sulfonic acid group.

The organic lakes may also be supported on an organic support such as rosin or aluminum benzoate, for example.

Among the organic lakes, mention may be made in particular of those known under the following names: D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22

Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake. D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake. D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake and FD&C Yellow No. 6 Aluminum lake.

Mention may also be made of liposoluble dyes, such as, for example, Sudan Red, DC Red 17, DC Green 6, β-carotene, soybean oil, Sudan Brown, DC Yellow 11, DC Violet 2, DC Orange 5 and quinoline yellow.

The chemical substances corresponding to each of the organic colorants cited above are mentioned in the publication "International Cosmetic Ingredient Dictionary and Handbook", 1997 edition, pages 371 to 386 and 524 to 528, published by "The Cosmetic, Toiletries and Fragrance Association", the content of which is incorporated into the present patent application by way of reference.

The pigments may also have been subjected to a hydrophobic treatment.

The hydrophobic treatment agent may be chosen from silicones such as methicones, dimethicones, alkoxysilanes and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids, N-acylamino acids or salts thereof; lecithin, isopropyl triisostearyl titanate, and mixtures thereof.

The N-acylamino acids can comprise an acyl group containing from 8 to 22 carbon atoms, such as, for example, a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above in particular denotes an alkyl group containing from 1 to 30 carbon atoms and preferably containing from 5 to 16 carbon atoms.

Hydrophobically treated pigments are described in particular in patent application EP-A-1 086 683.

Nacres

For the purposes of the present patent application, the term "nacre" means coloured particles of any shape, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride.

They may also be mica particles, at the surface of which are superposed at least two successive layers of metal oxides and/or of organic colorants.

The nacres may more particularly have a yellow, pink, red, bronze, orangey, brown, gold and/or coppery colour or tint.

As illustrations of nacres that may be introduced as interference pigments into the first composition, mention may be made of the gold-colored nacres sold in particular by the company BASF under the name Brilliant gold 212G® colorant (Timica® colorant), Gold 222C (Cloisonne® colorant), Sparkle Gold® colorant (Timica® colorant), and Monarch gold 233X® colorant (Cloisonne® colorant): the bronze nacres sold in particular by the company Merck under the name Bronze Fine® colorant (17384) (Colorona®, colorant) and Bronze® colorant (17353) (Colorona®, colorant) and by the company BASF under the name Super Bronze® colorant (Cloisonne®, colorant); the orange nacres sold in particular by the company BASF under the name Orange 363C® colorant (Cloisonnet® colorant) and by the company Merck under the name Passion Orange® colorant (Colorona® colorant) and Matte Orange® colorant (17449) (Microna® colorant); the brown tinted nacres sold in particular by the company Engelhard under the name Nu-antique copper 340XBR® colorant (Cloisonne® colorant) and Brown CL4509® colorant (Chroma-litel colorant); the copper-tinted nacres sold in particular by the company BASF under the name Copper 340A® colorant (Timica® colorant); the red-tinted nacres sold in particular by the company Merck under the name Sienna Fine® % colorant (17386) (Colorona® colorant); the yellow-tinted nacres sold in particular by the company BASF under the name Yellow (4502)® colorant (Chromalite® colorant): the gold-tinted red nacres sold in particular by the company BASF under the name Sunstone G0129® colorant (Gemtone® colorant); the pink nacres sold in particular by the company BASF under the name Tan opal G005® colorant (Gemtone® colorant): the gold-tinted black nacres sold in particular by the company BASF under the name Nu antique bronze 240 AB® colorant (Timica® colorant), the blue nacres sold in particular by the company Merck under the name Matte Blue® colorant (17433) (Microna® colorant), the silvery-tinted white nacres sold in particular by the company Merck under the name Xirona Silver® colorant, and the golden-green pink-orange nacres sold in particular by the company Merck under the name Indian Summer® colorant (Xirona® X colorant), and mixtures thereof Goniochromatic Pigments For the purposes of the present invention, the term "goniochromatic pigment" denotes a pigment which makes it possible to obtain, when the composition is spread onto a support, a colour trajectory in the a*b* plane of the CIE 1976 colorimetric space that corresponds to a variation Dh° in the hue angle h° of at least 20° when the angle of observation relative to the normal is varied between 0° and 80°, for an incident light angle of 45°.

The color trajectory may be measured, for example, using an Instrument Systems brand spectrogonioreflectometer of reference GON 360® Goniometer, after the composition has been spread in fluid form to a thickness of 300 µm using an automatic spreader onto an Erichsen brand contrast card of reference Typ 24/5® spreader, the measurement being taken on the black background of the card.

The goniochromatic pigment may be chosen, for example, from multilayer interference structures and liquid-crystal colouring agents.

In the case of a multilayer structure, it may comprise, for example, at least two layers, each layer being made, for example, from at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers and combinations thereof.

The multilayer structure may or may not have, relative to a central layer, symmetry in the chemical nature of the stacked layers.

Different effects are obtained depending on the thickness and the nature of the various layers.

Examples of symmetrical multilayer interference structures are, for example, the following structures: $Fe_2O_3/SiO_2/Fe_2O_3/SiO_2/Fe_2O_3$, a pigment having this structure being sold under the name Sicopearl by the company BASF; $MoS_2/SiO_2$/mica-oxide/$SiO_2/MoS_2$; $Fe_2O_3/SiO_2$/mica-oxide/$SiO_2/Fe_2O_3$; $TiO_2/SiO_2fTiO_2$ and $TiO_2/Al_2O_3/TiO_2$, pigments having these structures being sold under the name Xirona by the company Merck.

The liquid-crystal coloring agents comprise, for example, silicones or cellulose ethers onto which are grafted mesomorphic groups. Examples of liquid-crystal goniochromatic particles that may be used include, for example, those sold by the company Chenix and also those sold under the name Helicone® HC particles by the company Wacker.

Goniochromatic pigments that may also be used include certain nacres, pigments with effects on a synthetic substrate, in particular a substrate such as alumina, silica, borosilicate, iron oxide or aluminum, or interference flakes obtained from a polyterephthalate film.

By way of nonlimiting examples of goniochromatic pigments, mention may in particular be made, alone or in mixtures, of SunShine® goniochromatic pigments sold by SunChemicals, Cosmicolor Celeste® pigments from Toyo Aluminium K.K., Xirona® pigments from Merck and Reflecks Multidimensions® pigments from BASF.

Optionally, these particles may comprise or be covered with optical brightener(s) (or organic white fluorescent substances).

Optical brighteners are compounds well known to a person skilled in the art. Such compounds are described in "Fluorescent Whitening Agent, Encyclopedia of Chemical Technology, Kirk-Othmer", vol. 11, pp. 227-241, $4^{th}$ Edition, 1994, Wiley.

Their use in cosmetics in particular exploits the fact that they consist of chemical compounds having fluorescence properties, which absorb in the ultraviolet region (maximum absorption at a wavelength of less than 400 nm) and re-emit energy by fluorescence for a wavelength of between 380 nm and 830 nm. They may be defined more particularly as compounds that absorb essentially in the UVA region between 300 and 390 nm and re-emit essentially between 400 and 525 nm. Their lightening effect is based more particularly on an emission of energy between 400 and 480 nm, which corresponds to an emission in the blue part of the visible region, which contributes to lightening the skin visually when this emission takes place on the skin.

Optical brighteners that are in particular known include stilbene derivatives, in particular polystyrylstilbenes and triazinylstilbenes, coumarin derivatives, in particular hydroxycoumarins and aminocoumarins, oxazole, benzoxazole, imidazole, triazole and pyrazoline derivatives, pyrene derivatives, porphyrin derivatives and mixtures thereof.

The optical brighteners that can be used may also be in the form of copolymers, for example of acrylates and/or methacrylates, grafted with optical brightener groups as described in application FR 99 10942.

According to a preferred embodiment, the colorant used in the present invention is chosen from metal oxide pigments, organic lakes, synthetic or natural water-soluble dyes and mixtures thereof.

According to a particularly preferred embodiment, the colorant(es) used in the present invention is chosen from Orange 4, Red 6, Red 28 lake, Red 7, Blue 1 lake, or mixtures thereof.

The colorant can be present in an amount ranging from 3% to 20% by weight, preferably, 5% to 16% by weight, more preferably 6% to 12% by weight, relative to the total weight of the composition.

Siloxysilicate

In a preferred embodiment, the composition according to the present invention further comprises a siloxysilicate resin.

As siloxysilicate resins, mention may be made of trimethylsiloxysilicate (TMS) resins, optionally in the form of powders.

Preferably, the siloxysilicate resin is a trimethylsiloxysilicate of formula $[(CH_3)_3SiO]_x(SiO_{4/2})_y$(MQ units) in which x and y are integers ranging from 50 to 80.

Such resins are marketed under the reference SR 1000® resin by the company MOMENTIVE PERFORMANCE MATERIALS or under the reference TMS 803® resin by the company Wacker. Mention may also be made of the trimethylsiloxysilicate resins marketed in a solvent such as cyclomethicone, sold under the name KF-7312J® resin by the company Shin-Etsu, and DC 749® resin and DC 5939® resin by the company Dow Corning.

The inventors have unexpected discovered that the composition comprising siloxysilicate, especially trimethylsiloxysilicate resin according to the present invention has good wear resistance, low color transfer as well as good shininess.

Preferably, the siloxysilicate, especially trimethylsiloxysilicate resin is present in amount ranging from 0.5% to 20% by weight, more particularly from 1% to 15% by weight and preferably from 1% to 10% by weight, relative to the total weight of the composition according to the present invention.

Additives

In a particular embodiment, an anhydrous composition according to the present invention may further comprise at least one additive usually used in the field under consideration. In particular the additive is chosen from gums, anionic, cationic, amphoteric or nonionic surfactants, silicone surfactants, resins, thickening agents, dispersants, antioxidants, preserving agents, fragrances, neutralizers, antiseptics, additional cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the present invention such that the advantageous properties of the composition used according to the present invention are not, or are not substantially, adversely affected by the envisaged addition.

According to a preferred embodiment, the present invention relates to an anhydrous composition for caring for and/or making up keratin materials comprising:

a) at least one wax chosen from synthetic wax, paraffin, microcrystalline wax, or mixtures thereof;

b) at least one colorant chosen from metal oxide pigments, organic lakes, synthetic or natural water-soluble dyes and mixtures thereof;
c) 10%~40% by weight of at least one non-volatile non-phenyl silicone oil chosen in particular from silicones of formula (I):

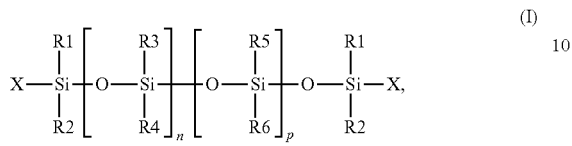

in which:
$R_1$, $R_2$, $R_5$, and $R_6$ are, together or separately, an alkyl radical containing from 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p are integers chosen so as to have a fluid compound, in particular of which the viscosity at 25° C. is between 100 centistokes (cSt) and 1,000 cSt, relative to the total weight of the composition;
d) at least one non-volatile hydrocarbon-based oil chosen from hydrogenated polyisobutenes, octyldodecyl neopentanoate, stearyl heptanoate, stearyl caprylate, vinylpyrrolidone/1-hexadecene copolymer and at least one phenyl silicone oil chosen from phenyl silicone oils not having a dimethicone fragment corresponding to formula (III) below:

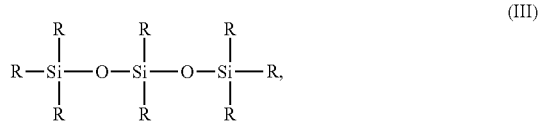

wherein at least 3, at least 4 or at least 5 radicals R represent a phenyl radical, the remaining radical R represent methyls, more preferably trimethylpentaphenyltrisiloxane or tetramethyltetraphenyltrisiloxane;
e) reaction product of vinyl MQ resin, and poly(methylhydrogen)dimethyl siloxane and optionally, $C_{10}$-$C_{24}$ unsaturated linear or branched alkene in dimethicone; and
f) trimethylsiloxysilicate of formula $[(CH_3)_3SiO]_x(SiO_{4/2})_y$ (MQ units) in which x and y are integers ranging from 50 to 80.

Galenic Form

The composition of the present invention is suitable to be used as a skin care, make up or cosmetic treatment product. More particularly, the composition of the present invention is in the form of make-up product such as lipstick and so on.

The composition according to the present invention may be prepared in a conventional manner.

The terms "between" and "ranging from" used herein should be understood as including the limits.

The present invention also relates to a process for caring for/making up keratin materials such as the skin and the lips, preferably the lips, by applying the anhydrous composition as described above to the keratin materials.

Unless defined otherwise, all technical and scientific terms used herein have the same meaning as commonly understand by one of ordinary skill in the art to which the present invention pertains.

The examples that follow are given as non-limiting illustrations of the present invention. The percentages are weight percentages.

EXAMPLES

Formulation Examples

Lipsticks with the following formulas are prepared (the contents are expressed as weight percentages of active material, unless otherwise indicated):

| Type | INCI US | Invention example 1 | Invention example 1 | Comparative example 2 |
|---|---|---|---|---|
| DYE/PIGMENT | ORANGE 4 (UNICERT ® ORANGE K7011-J from SENSIENT) | 0.292 | 0.292 | 0.292 |
| DYE/PIGMENT | BLUE 1 LAKE (09901 FD&C BLUE # 1 LAKE ® from SENSIENT) | 0.077 | 0.077 | 0.077 |
| DYE/PIGMENT | RED 6 (C19-6619 SUNCROMA ® D&C RED 6 NA SALT from SUN) | 3.726 | 3.726 | 3.726 |
| DYE/PIGMENT | RED 7 (UNIPURE ® RED LC 3079 OR ® from SENSIENT) | 1.98 | 1.98 | 1.98 |
| DYE/PIGMENT | RED 28 LAKE (SUNCROMA D&C RED 28 AL LAKE C14-6623 from SUN) | 0.624 | 0.624 | 0.624 |
| FATTY COMPOUND | STEARYL HEPTANOATE (and) STEARYL CAPRYLATE(DUB SOLIDE ® wax from STEARINERIE DUBOIS) | 5 | 5 | 5 |
| FATTY COMPOUND | OCTYLDODECYL NEOPENTANOATE | 11.671 | 11.671 | 11.671 |
| FATTY COMPOUND | PARAFFIN (and) MICROCRYSTALLINE WAX (and) SYNTHETIC WAX (PARACERA 30540 ® wax from PARAMELT) | 2.56 | 2.56 | 2.56 |
| POLYMER | HYDROGENATED POLYISOBUTENE (PARLEAM ® resin from NOF CORPORATION) | 10 | 10 | 10 |
| POLYMER | SUCROSE ACETATE ISOBUTYRATE (SUSTANE SAIB ® FOOD GRADE KOSHER resin from EASTMAN CHEMICAL) | 5.5 | 5.5 | 0 |

-continued

| Type | INCI US | Invention example 1 | Invention example 1 | Comparative example 2 |
|---|---|---|---|---|
| POLYMER | HYDROGENATED POLYISOBUTENE (PARLEAM LITE ® resin from NOF CORPORATION) | 10.98 | 10.98 | 10.98 |
| POLYMERIC FILLER | SYNTHETIC WAX (CIREBELLE 108 ® wax from CIREBELLE) | 7.69 | 7.69 | 7.69 |
| SILICON | DIMETHICONE (XIAMETER PMX-200 ® SILICONE FLUID 1000CS ® silicone from DOW CORNING (DOW CHEMICAL)) | 20.4 | 20.4 | 20.4 |
| SILICON | TRIMETHYLSILOXYSILICATE (SR 1000 ® silicone from MOMENTIVE PERFORMANCE MATERIALS) | 2.75 | 0 | 2.75 |
| SILICON | PEG-10 DIMETHICONE (KF-6017 ® silicone from SHIN ETSU) | 5 | 5 | 5 |
| SILICON | TRIMETHYL PENTAPHENYL TRISILOXANE (DOW CORNING PH-1555 HRI ®) COSMETIC FLUID from DOW CORNING (DOW CHEMICAL)) | 9 | 9 | 9 |
| SILICON | DIMETHICONE (and) DIMETHICONE/VINYLTRIMETHYLSILOXYSILICATE CROSSPOLYMER* | 2.75 | 2.75 | 2.75 |
|  | VP/HEXADECENE COPOLYMER ® silicone (ANTARON V 216 from ISP (ASHLAND)) | 0 | 2.75 | 5.5 |

*The amount indicated includes the amount of dimethicone therein.

Protocol of Preparation

The lipsticks are prepared following the steps of:
i) Mixing all the ingredients under 93° C., stirring the mixture at 300 r/min by IKA Blender Euro—ST P CV S25 model until homogeneous,
ii) Pouring the homogenized mixture into a lip stick mold at 93° C. leaving the mixture in the mold under 25° C. until solidation; and
iii) Demolding the solid mixture from the lip stick mold.

Evaluation Example

Evaluation on hardness of the lipsticks, stability of the shape of the lipsticks, spreadability of the lipsticks, color transfer, wear of color, non-sticky and non-dry feeling after application of the lipsticks are performed.

Hardness is evaluated according to the protocol described previously.

Stability of the shape is evaluated using crash test, by following steps:
heat the composition to 38° C. for 24 hours;
apply the composition to the lips under the heated temperature.

Spreadability is evaluated by 5 experts by the following steps:
repeatedly apply the composition three times on the same area of the forearm using the same force:
weigh the weight loss of the composition;
measure the size of the area on the forearm where the composition is applied;
calculate the weight loss per square centimeter.

The non-sticky and non-dry feeling is evaluated by 5 experts by the following steps:
Firstly, repeatedly apply the compositions according to invention and comparative examples, respectively, three times on the same area of the lips using the same force.

Then comments or scores are given by the experts on the properties mentioned above.
5: very good;
4: basically good;
3: acceptable;
2: slightly poor and not acceptable;
1: poor, not acceptable.

Color transfer is evaluated by 5 experts by the following steps:

Firstly, repeatedly apply the compositions according to invention and comparative examples, respectively, three times on the same area of the lips using the same force; wait for 5 min, then kiss a tissue, check color transfer on tissue. The less the color transfer, the better.

Then comments or scores are given as follows.
5: low;
3: medium;
1: high.

Wear of color is measured as follows:

Apply 7.3 mg lipstick on bioskin within a circle (d=2.5 cm). Choose 10 mm circle mode of VS450 spectrophotometer to focus on sample center to measure the L*, a* and b*. Then put a tissue paper on top of the sample, use Texture analyzer with 2200 g pressure to press the tissue paper, then remove the tissue paper, and measure L*, a* and b* of the sample again. Based on the color info obtained before & after tissue challenge, calculate the ΔE.

The resulted are summarized in the following table 1:

TABLE 1 properties of invention compositions and comparative examples

|  | Invention Example 1 | Invention Example 2 | Comparative Example 1 |
|---|---|---|---|
| Color transfer | 5 | 5 | 3 |
| Wear of color(ΔE) | 2.67 | 4.39 | 4.11 |
| Non-sticky and non-dry feeling | 5 | 5 | 5 |
| Hardness | 5 | 5 | 5 |
| Stability of the shape | 5 | 5 | 5 |
| Spreadability | 5 | 5 | 5 |
| Shineness | Good | Good | normal |

It is observed that the compositions according to invention examples 1-2 demonstrated low color transfer, and good sensory upon application, while the composition according to comparative example 1 showed medium color transfer. In addition, the composition according to invention example 1 also demonstrated good wear resistance.

The invention claimed is:

1. An anhydrous composition adapted for caring for and/or making up keratin materials, the composition comprising:
   (a) a non-volatile non-phenyl silicone oil in a range of from 10 to 40 wt. % by weight, relative to a total composition weight;
   (b) a non-volatile hydrocarbon-based oil and/or phenyl silicone oil;
   (c) a high viscosity $C_2$-$C_6$ carboxylic acid ester of sucrose; and
   (d) a reaction product of an unsaturated-functional silicone resin, an Si—H functional organopolysiloxane crosslinker bearing pendant hydrido functionality, and optionally, an unsaturated hydrocarbon comprising four or more carbon atoms, in a low viscosity organopolysiloxane.

2. The composition of claim 1, further comprising: a wax and/or colorant.

3. The composition of claim 1, wherein the non-volatile non-phenyl silicone oil (a) has formula (I):

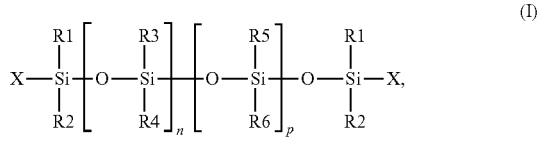

wherein:
$R_1$, $R_2$, $R_5$, and $R_6$ are each independently an alkyl radical comprising from 1 to 6 carbon atoms,
$R_3$ and $R_4$ are each independently an alkyl radical comprising from 1 to 6 carbon atoms, a vinyl radical, an amine radical, or a hydroxyl radical,
X is an alkyl radical comprising from 1 to 6 carbon atoms, a hydroxyl radical, or an amine radical,
n and p are integers chosen so as to have a fluid compound, in which the viscosity at 25° C. is between 100 centistokes (cSt) and 1000 cSt.

4. The composition of claim 1, further comprising: the non-volatile hydrocarbon-based oil, comprising hydrogenated polyisobutylene, hydrogenated polydecene, synthetic ester or vinylpyrrolidone, and/or copolymer of vinylpyrrolidone.

5. The composition of claim 1 further comprising: a non-volatile phenyl silicone oil, wherein the non-volatile phenyl silicone oil has no dimethicone fragment of formula (III) below:

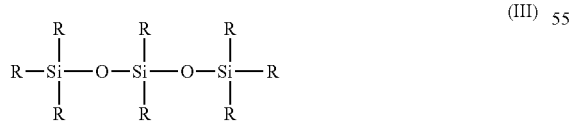

wherein at least 3 radicals R are a phenyl radical, and the remaining radical R are methyl.

6. The composition of claim 1, wherein the high viscosity $C_2$-$C_6$ carboxylic acid ester has a viscosity of at least 10,000 cps at room temperature.

7. The composition of claim 1, wherein the reaction product of comprises a reaction product of vinyl MQ resin, poly(methylhydrogen)dimethylsiloxane, and optionally, $C_{10}$-$C_{24}$ unsaturated linear or branched alkene in dimethicone.

8. The composition of claim 2, comprising:
   an animal wax, vegetable wax, mineral wax, synthetic wax, and/or silicon wax.

9. The composition of claim 2, comprising:
   a metal oxide pigment, organic lake, synthetic water-soluble dye, and/or natural water-soluble dye.

10. The composition of claim 1, further comprising:
    a siloxysilicate resin.

11. The composition of claim 10, wherein the siloxysilicate resin comprises a trimethylsiloxysilicate of formula

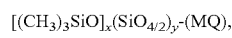

in which x and y are integers in a range of from 50 to 80.

12. The composition of claim 1, wherein the non-volatile non-phenyl silicone oil is present in a range of from 10 to 40 wt. %, relative to the total composition weight.

13. The composition of claim 1, wherein the non-volatile hydrocarbon-based oil and/or phenyl silicone oil is present in a total content in a range of from 30 to 70 wt. %, relative to the total composition weight.

14. An anhydrous composition adapted for caring for and/or making up keratin materials, the composition comprising:
    (a) a synthetic wax, paraffin, and/or microcrystalline wax;
    (b) a metal oxide pigment, organic lake, synthetic water-soluble dye, and/or natural water-soluble dye;
    (c) a non-volatile non-phenyl silicone oil of formula (I), in a range of from 10 to 40 wt. %:

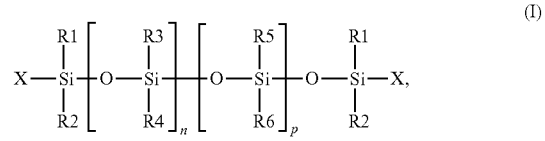

$R_1$, $R_2$, $R_5$, and $R_6$ independently being an alkyl radical comprising from 1 to 6 carbon atoms, $R_3$ and $R_4$ independently being an alkyl radical comprising from 1 to 6 carbon atoms, a vinyl radical, an amine radical, or a hydroxyl radical, X being an alkyl radical comprising from 1 to 6 carbon atoms, a hydroxyl radical, or an amine radical, and n and p being integers selected so as to have a fluid compound, in which the viscosity at 25° C. is in a range of from 100 to 1000 cSt;
    (d) a non-volatile hydrocarbon-based oil comprising a hydrogenated polyisobutene, octyldodecyl neopentanoate, stearyl heptanoate, stearyl caprylate, vinylpyrrolidone/1-hexadecene copolymer, and a phenyl silicone oil not having a dimethicone fragment of formula (III):

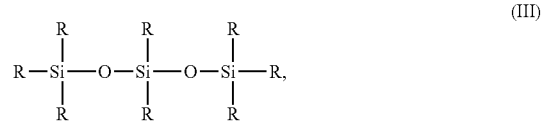

at least 3 radicals R being a phenyl radical, the remaining radical R being methyl;

(e) a reaction product of vinyl MQ resin, poly(methylhydrogen)dimethylsiloxane and optionally, $C_{10}$-$C_{24}$ unsaturated linear or branched alkene in dimethicone; and (f) a trimethylsiloxysilicate of formula $[(CH_3)_3SiO]_x(SiO_{4/2})_y$-(MQ), in which x and y are integers in a range of from 50 to 80; and (g) a high viscosity $C_2$-$C_6$ carboxylic acid ester of sucrose.

15. A process of caring for and/or making up keratin materials, the process comprising:
    applying the composition of claim 1 to the keratin materials.

16. The composition of claim 1, wherein the reaction product (d) comprises the unsaturated hydrocarbon.

17. The composition of claim 1, wherein the high viscosity $C_2$-$C_6$ carboxylic acid ester comprises sucrose tetraoleate, sucrose pentaoletate, sucrose hexaoleate, sucrose hepatoleate, and/or sucrose octaoleate.

18. The composition of claim 1, wherein the high viscosity $C_2$-$C_6$ carboxylic acid ester comprises a mixed ester of acetic acid, isobutyric acid, and sucrose.

19. The composition of claim 1, wherein the high viscosity $C_2$-$C_6$ carboxylic acid ester is sucrose diacetate hexakis (2-methylpropanoate).

20. The composition of claim 1, wherein the high viscosity $C_2$-$C_6$ carboxylic acid ester has a viscosity of about 100,000 cps at 30° C. and a refractive index of about 1.5 at 20° C., and
    wherein the high viscosity $C_2$-$C_6$ carboxylic acid ester is present in the composition in a range of from 4 to 10 wt. %, relative to the total weight of the composition.

* * * * *